United States Patent
Dees, Jr. et al.

(10) Patent No.: US 8,845,745 B2
(45) Date of Patent: Sep. 30, 2014

(54) ORTHOPAEDIC IMPLANT SYSTEM AND FASTENERS FOR USE THEREIN

(75) Inventors: Roger Ryan Dees, Jr., Senatobia, MS (US); Paul Charles Crabtree, Jr., Nesbit, MS (US)

(73) Assignee: Smith & Nephew, Inc., Memphis, TN (US)

( * ) Notice: Subject to any disclaimer, the term of this patent is extended or adjusted under 35 U.S.C. 154(b) by 127 days.

(21) Appl. No.: 13/150,500

(22) Filed: Jun. 1, 2011

(65) Prior Publication Data
US 2011/0295377 A1 Dec. 1, 2011

Related U.S. Application Data

(60) Provisional application No. 61/350,346, filed on Jun. 1, 2010.

(51) Int. Cl.
*A61F 2/38* (2006.01)
*A61F 2/28* (2006.01)
*A61F 2/30* (2006.01)

(52) U.S. Cl.
CPC ............ *A61F 2/3868* (2013.01); *A61F 2/3886* (2013.01); *A61F 2/389* (2013.01); *A61F 2002/2892* (2013.01); *A61F 2002/3051* (2013.01); *A61F 2002/30528* (2013.01); *A61F 2002/30518* (2013.01)
USPC ..................................... 623/20.32; 623/20.33

(58) Field of Classification Search
CPC .................... A61F 2/389; A61F 2002/2892
USPC .......... 623/20.15, 20.32, 20.33, 20.14, 20.34, 623/20.28–20.3
See application file for complete search history.

(56) References Cited

U.S. PATENT DOCUMENTS

| | | | | |
|---|---|---|---|---|
| 5,358,527 | A | * | 10/1994 | Forte ........................... 623/20.27 |
| 5,824,103 | A | * | 10/1998 | Williams .................... 623/20.32 |
| 6,004,352 | A | * | 12/1999 | Buni ........................... 623/20.33 |
| 6,972,039 | B2 | * | 12/2005 | Metzger et al. ............. 623/20.29 |

(Continued)

FOREIGN PATENT DOCUMENTS

| | | |
|---|---|---|
| EP | 1025818 A2 | 8/2000 |
| WO | WO9709939 A1 | 3/1997 |
| WO | WO9966864 A1 | 12/1999 |
| WO | WO0124741 A1 | 4/2001 |

OTHER PUBLICATIONS

International Search Report for International Application No. PCT/US2011/038712, mailed Feb. 9, 2012, 4 pages.

*Primary Examiner* — David H Willse
*Assistant Examiner* — Javier Blanco
(74) *Attorney, Agent, or Firm* — Fish & Richardson P.C.

(57) ABSTRACT

Orthopaedic assemblies including a tibial component and one of a fixed tibial insert or a rotatable tibial insert. The assemblies may include structure to prevent undesired movement between the tibial component and insert. For example, a retaining tab may be provided on the tibial component that couples to a tab opening on a surface of the tibial insert (either the fixed or rotatable insert). When assembled, the retaining tab may be covered to avoid possible irritation to the patient's surrounding anatomy. The fixed tibial insert may be provided with a tab opening that provides a minimal amount clearance with the retaining tab to help prevent rotation of the fixed tibial insert. The rotatable tibial insert may be provided with a tab opening with more clearance with the retaining tab to allow at least some rotation with the tibial component.

30 Claims, 14 Drawing Sheets

(56) References Cited

U.S. PATENT DOCUMENTS

| | | | |
|---|---|---|---|
| 2004/0215345 A1* | 10/2004 | Perrone et al. | 623/20.32 |
| 2005/0246027 A1* | 11/2005 | Metzger et al. | 623/20.15 |
| 2005/0283253 A1* | 12/2005 | Coon et al. | 623/20.35 |
| 2006/0100714 A1* | 5/2006 | Ensign | 623/20.16 |
| 2007/0129808 A1 | 6/2007 | Justin et al. | |
| 2008/0091271 A1* | 4/2008 | Bonitati et al. | 623/20.34 |

* cited by examiner

ORTHOPAEDIC IMPLANT SYSTEM AND FASTENERS FOR USE THEREIN

CROSS REFERENCE TO RELATED APPLICATIONS

This application claims the benefit of U.S. Provisional Patent Application Ser. No. 61/350,346 entitled "Orthopaedic Implant System and Fasteners for use Therein" and filed Jun. 1, 2010, the entire contents of which are hereby incorporated by this reference.

RELATED FIELDS

Apparatus and methods for coupling components of orthopaedic implants together are described herein.

BACKGROUND OF THE INVENTION

Orthopaedic implants, including for instance knee implants, can be modular in nature and include several components. For instance, many knee implants include a femoral implant and a tibial implant. The tibial implant may include a base tibial component and one or more inserts. After bone resectioning, the tibial component is positioned on the patient's tibia and the femoral component is positioned on the patient's femur. The tibial insert is secured to or captured by the tibial component, and includes a superior surface for contact with one or two (depending on the type of femoral implant) condylar surfaces of the femoral component (or the native femoral condyles). In use, the condylar surfaces of the femoral component and/or native femur will articulate on the superior surface of the tibial insert as the knee joint flexes and extends.

Tibial inserts may be either fixed or rotatable. A rotatable tibial insert rotates with respect to the tibial component (which is fixedly secured to the tibia) as the knee joint flexes and extends. On the other hand, a fixed tibial insert is not intended to rotate with respect to the tibial component when the knee joint flexes and extends. The type of implant chosen for a particular patient, including whether a fixed or rotating tibial insert is used, depends on a number of factors, including the condition of the patient's bones, ligamenture and other anatomy.

The components of a knee implant are subject to large loads and other forces in vivo that are applied over many cycles throughout the implant's useful life. Accordingly, it is important that the components of the tibial implant, including the tibial component and the tibial insert, be appropriately coupled to one another such that they do not separate or otherwise move in unintended manners once implanted in the patient.

Prior systems of coupling the components have several problems. First, some prior systems use coupling mechanisms that are "exposed" in that when the knee joint is in flexion, edges, protrusions or other surfaces of the coupling mechanism contact or impinge on the patient's surrounding anatomy. Such contact or impingement may be painful to the patient, may destroy or damage the ligamenture, bone and/or other anatomy, or may damage the locking component. Second, many prior systems do not provide adequate constraints against movement (both rotational and vertical) of tibial inserts with respect to their associated tibial components, especially as the implant is cycled numerous of times. In some instances, prior systems can fail when the tibial insert "spins outs," "pulls out," or otherwise becomes dislocated with respect to the tibial component. Spin out refers to excessive rotation of the tibial insert (particularly for rotatable tibial inserts) such that the tibial insert becomes improperly oriented within the knee joint. Pull out refers to vertical separation between the tibial insert and the tibial component. Third, prior systems with fixed tibial inserts, in some instances, may undesirably allow at least some rotation of the fixed insert. Fourth, prior systems with fixed tibial inserts may use fasteners to secure the insert to the tibial component that may loosen and back out, thus un-coupling the insert from the tibial component.

Thus, there is a need in some instances for an orthopaedic implant that includes structure to couple a tibial insert to a tibial component, but that avoids contact with the patient's ligamenture, bone and other surrounding anatomy.

There is a need in some instances for an orthopaedic implant that minimizes excessive or undesirable rotation between the tibial insert and the tibial component.

There is a need in some instances for an orthopaedic implant that avoids vertical separation of the tibial insert from the tibial component.

There is a need in some instances for improved fasteners that will not loosen or back out of the tibial insert.

Finally, there is a need in some instances for a tibial component that may be used interchangeably with either a fixed tibial insert or a rotatable tibial insert.

SUMMARY

Certain embodiments described herein provide an orthopaedic assembly including a tibial component and one of a fixed tibial insert or a rotatable tibial insert. The assemblies may be provided with improved structure to couple the tibial insert to the tibial component to prevent spin out, pull out, other undesired rotations and/or translations, and/or irritation to the patient's surrounding anatomy.

The tibial components described herein may include a retaining tab with a hooked edge that couples to a tab opening on an inferior surface of the tibial insert (either the fixed insert or the rotatable insert). The retaining tab may be set back from the outermost anterior edge of the tibial component such that when assembled, a portion of the tibial insert covers the retaining tab. Thus, neither the retaining tab or the tab opening are exposed to the patient's surrounding anatomy, preventing possible pinch points and irritation when the knee is in flexion. The hooked edge of the retaining tab contacts an inner surface of the tibial insert to prevent vertical separation (or pull out) of the tibial insert from the tibial component.

Certain embodiments may also be provided with structure to prevent excessive or unwanted rotation between the tibial component and the tibial insert. For example, tibial inserts may be provided with tab openings (such as the tab openings described above) that receive the retaining tab of the tibial component and are structured in a manner to limit movement of the retaining tab in the tab opening. The fixed tibial insert may be provided with a tab opening conforming in at least some dimensions to the size and shape of the retaining tab, such that there is little to no clearance with the retaining tab, thus helping to prevent rotation of the fixed tibial insert. In contrast, the rotatable tibial insert may be provided with a relatively elongated tab opening, such that there is clearance with the retaining tab. This clearance may allow the rotatable tibial insert to rotate with respect to the tibial component.

Certain embodiments may also be provided with fasteners to further minimize any movement of the fixed tibial insert. Such fasteners may include a deformable portion that creates an interference fit with the fixed tibial insert. The interference fit will help retain the fastener within the fixed tibial insert even if the fastener rotates or otherwise becomes loose.

In accordance with some embodiments, there may be provided an orthopaedic implant comprising a first implant component, the first implant component comprising: a substantially planar mounting surface configured for mounting to a second implant component; a retaining tab extending upwardly away from the substantially planar mounting surface; and an angled opening configured to receive a fastener, wherein the angled opening extends downwardly from the substantially planar mounting surface at an angle that is non-perpendicular relative to the substantially planar mounting surface.

The angled opening may be angled away from the retaining tab.

The angled opening may be at least partially threaded.

The retaining tab may set back from an outer edge of the first implant component.

The retaining tab may comprise a hooked portion extending above the substantially planar mounting surface.

The hooked portion may extend away from the angled opening.

The retaining tab may comprise a substantially vertical portion and wherein the hooked portion extends from an upper end of the substantially vertical portion.

The hooked portion may be substantially horizontal relative to the substantially vertical portion.

The hooked portion may include an angled surface on an underside of the hooked portion.

The first implant component may comprise a tibial tray.

The orthopaedic implant may further comprise the second implant component, wherein the second implant component comprises a tibial insert, the tibial insert comprising an articular surface on a superior side of the tibial insert and a substantially planar mounting surface on an inferior side of the tibial insert.

The tibial insert may further comprise a tab opening configured to receive the retaining tab, the tab opening extending from the substantially planar mounting surface of the tibial insert.

The tab opening may further comprise an angled surface configured to confront the angled surface of the retaining tab.

The tibial insert may comprise an angled opening configured to receive the fastener, wherein the angled opening of the tibial insert extends away from the substantially planar mounting surface of the tibial insert at the same angle as the angled opening of the first implant component extends relative to the substantially planar mounting surface of the first implant component.

The orthopaedic implant may further comprise the fastener, wherein the fastener includes an interference portion configured to cause an interference fit with respect to at least one of the angled openings of the first implant component and the tibial insert.

In accordance with some embodiments, there may be provided an orthopaedic implant comprising: a tibial tray, wherein the tibial tray comprises a substantially planar tray surface and an angled opening configured to receive a fastener, wherein the angled opening extends downwardly from the substantially planar tray surface at an angle that is non-perpendicular relative to the substantially planar tray surface; and a tibial insert, wherein the tibial insert comprises an articular surface and a substantially planar mounting surface configured to abut the tray surface; wherein a retaining tab including a hooked edge extends from one of the tray surface and the mounting surface; wherein a tab opening including a recess extends into the other of the tray surface and the mounting surface; and wherein the hooked edge of the retaining tab is configured to engage the recess of the tab opening when the tibia insert is mounted to the tibia tray with the substantially planar mounting surface of the tibial insert in abutment with the tray surface of the tibial tray.

The tibial insert may be a mobile bearing insert and wherein the substantially planar mounting surface is a second articular surface.

The tibial insert may be a fixed insert; and wherein the orthopaedic implant further comprises the fastener configured to be received in the angled opening.

The retaining tab may extend from the tray surface; and wherein the hooked edge of the retaining tab and the angled opening extend away from one another.

In accordance with some embodiments, there may be provided an orthopaedic implant, comprising: a first orthopaedic component, the first orthopaedic component including an articular surface and a mating surface, wherein an opening extends from the mating surface of the first orthopaedic component at least partially through the first orthopaedic component; a second orthopaedic component, the second orthopaedic component including a mating surface configured to abut the mating surface of the first orthopaedic component, wherein a second opening extends from the mating surface of the second orthopaedic component at least partially through the second orthopaedic component; and a threaded fastener configured to secure the first orthopaedic component to the second orthopaedic component and to extend at least partially through the first and second openings, wherein the fastener includes a means for creating an interference fit with at least one of the first and second openings; wherein at least one of the first and second openings is partially threaded.

In accordance with some embodiments, there may be provided an orthopaedic implant, comprising: a first orthopaedic component, comprising a substantially planar mounting surface; and a second orthopaedic component, comprising a substantially planar mounting surface on a first side of the second orthopaedic component and a condylar articular surface on a second side of the orthopaedic component; wherein the first orthopaedic component is a tibial tray and the second orthopaedic component is a tibial insert; wherein the second orthopaedic component is configured to be secured to the first orthopaedic component in a rotating fashion; wherein an arcuate retaining tab including a hooked edge extends from one of the mounting surfaces of the first and second orthopaedic components; wherein an arcuate tab opening including a recess extends into the other of the mounting surfaces of the first and second orthopaedic components; wherein the arcuate tab opening is configured to receive the arcuate retaining tab when the second orthopaedic component is secured to the first orthopaedic component such that the arcuate retaining tab can rotate in the arcuate tab opening along a rotational arc; and wherein the arcuate tab opening extends along a greater portion of the rotational arc than the arcuate retaining tab.

The arcuate retaining tab may extend from the mounting surface of the first orthopaedic component; and wherein the arcuate retaining tab is set back from an outer edge of the first orthopaedic component.

The orthopaedic implant may further comprise a post; wherein at least one of the first and second orthopaedic components is configured to receive the post; and wherein the second orthopaedic component is configured to rotate with respect to the first orthopaedic component about the post.

BRIEF DESCRIPTION OF THE DRAWINGS

The specification makes reference to the following appended figures, in which use of like reference numerals in different features is intended to illustrate like or analogous components.

DETAILED DESCRIPTION

FIGS. 1-23 illustrate structures and mechanisms for coupling tibial inserts and tibial components together. Although the orthopaedic implants shown and described herein are for knee joints, the same concepts could potentially be applied to implants for other joints or orthopaedic implants. FIGS. 3-16 illustrate embodiments of implants that include fixed tibial inserts 40 or other types of fixed constructs, whereas FIGS. 17-23 illustrate embodiments that include rotatable tibial inserts 90. In the embodiments shown, the same tibial component 10 may be used, thus providing for interchangability between tibial inserts 40, 90.

Figure 1:
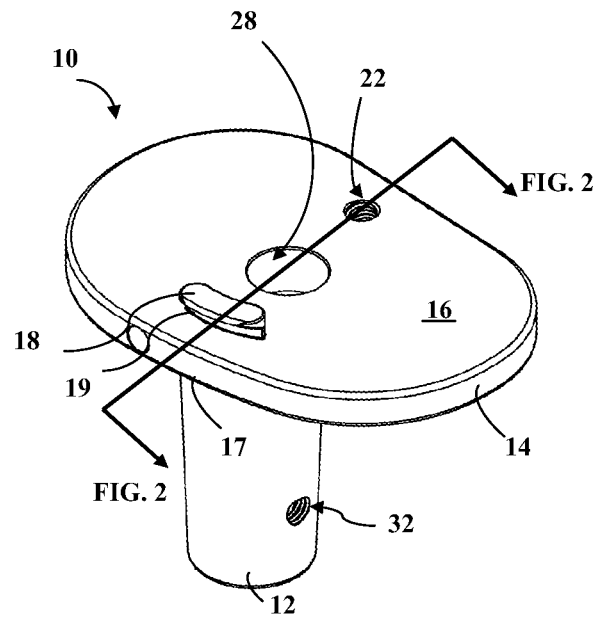
FIG. 1 is a perspective view of a tibial component.
Figure 2:
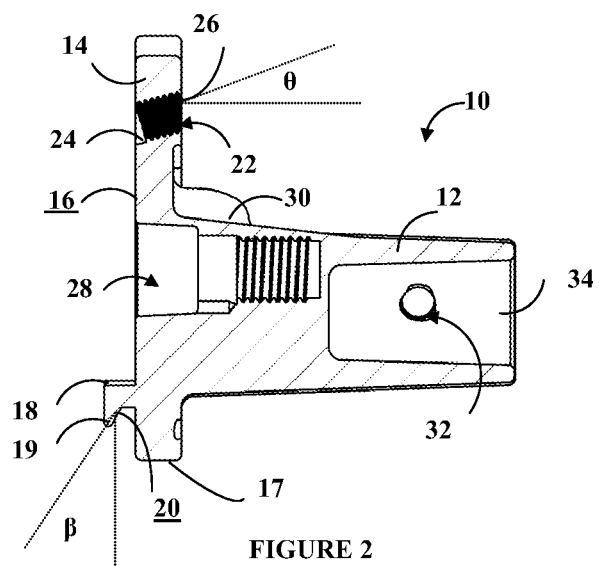
FIG. 2 is a cross-sectional view of the tibial component of FIG. 1 taken along line FIG. 2-FIG. 2.
Figure 3:
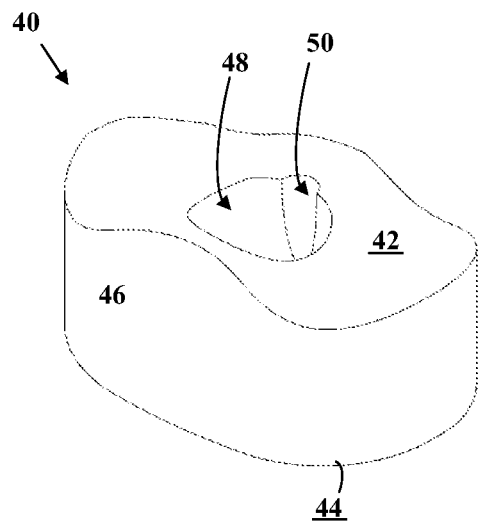
FIG. 3 is a perspective view of a fixed insert.
Figure 4:
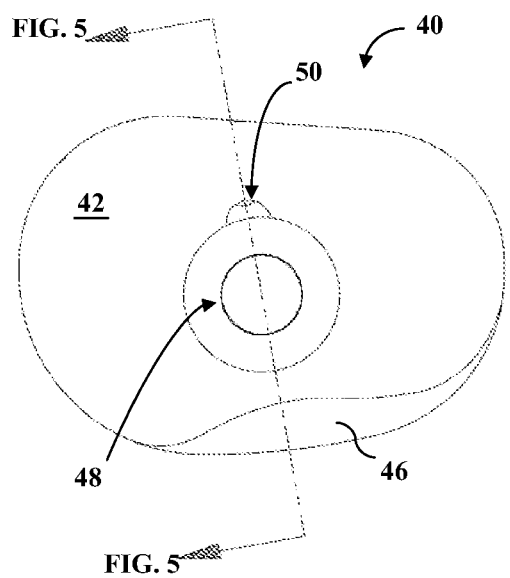
FIG. 4 is a top plan view of the fixed insert of FIG. 3.

FIGS. 1-2 show a tibial component 10 including a stem portion 12 and a tibial tray 14. The stem portion 12 may be dimensioned to couple with structure (not shown) that is inserted into a patient's intramedullary canal (and itself may be inserted into the intramedullary canal). Thus, for example, the stem portion 12 may include at least one opening 32 and/or recess 34 that facilitates coupling the tibial component 10 to other structure. The stem portion 12 may include fins 30 or other structure such as bone-engaging fluting, porous materials to promote bony in-growth or other features to facilitate securing the tibial component in the proximal tibia.

The tibial tray 14 shown in the figures rests on top of the patient's resected tibia. The tibial tray 14 may include a tray surface 16 that is generally planar and that contacts a tibial insert 40, 90 as described below. The tibial tray 14 shown also includes an outermost anterior edge 17.

Figure 8A:
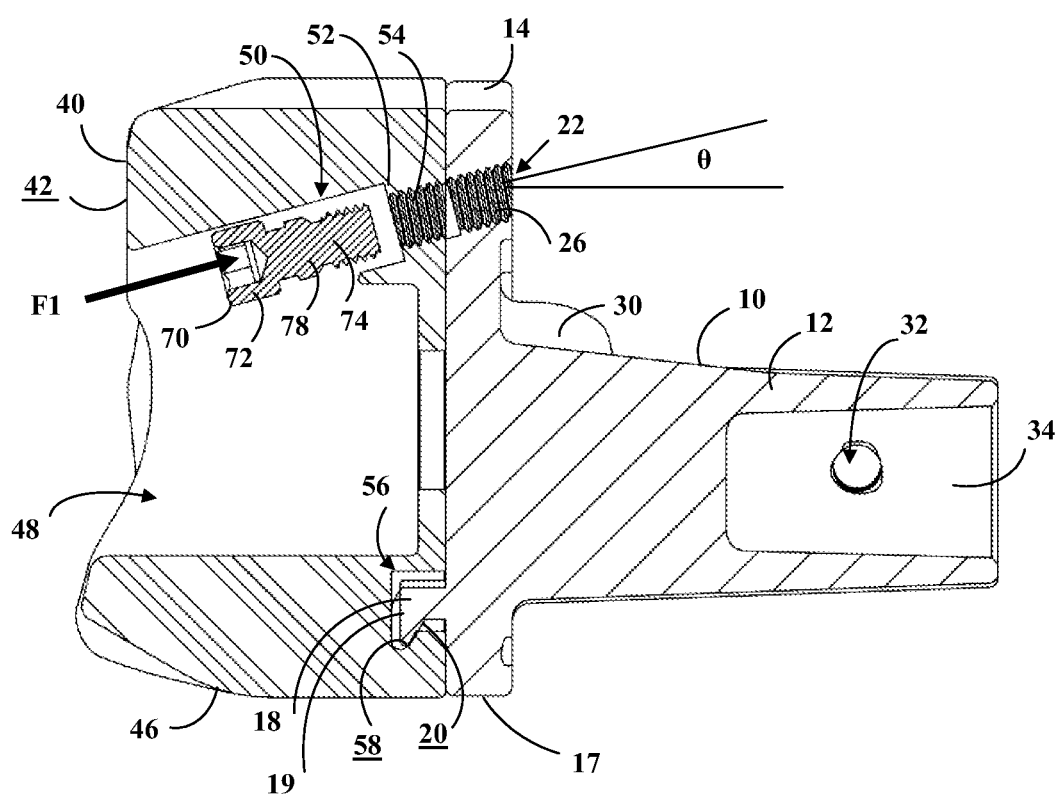
FIGS. 8A-B are cross-sectional views of the assembly of FIG. 7 taken along line FIG. 8-FIG. 8.
Figure 8B:
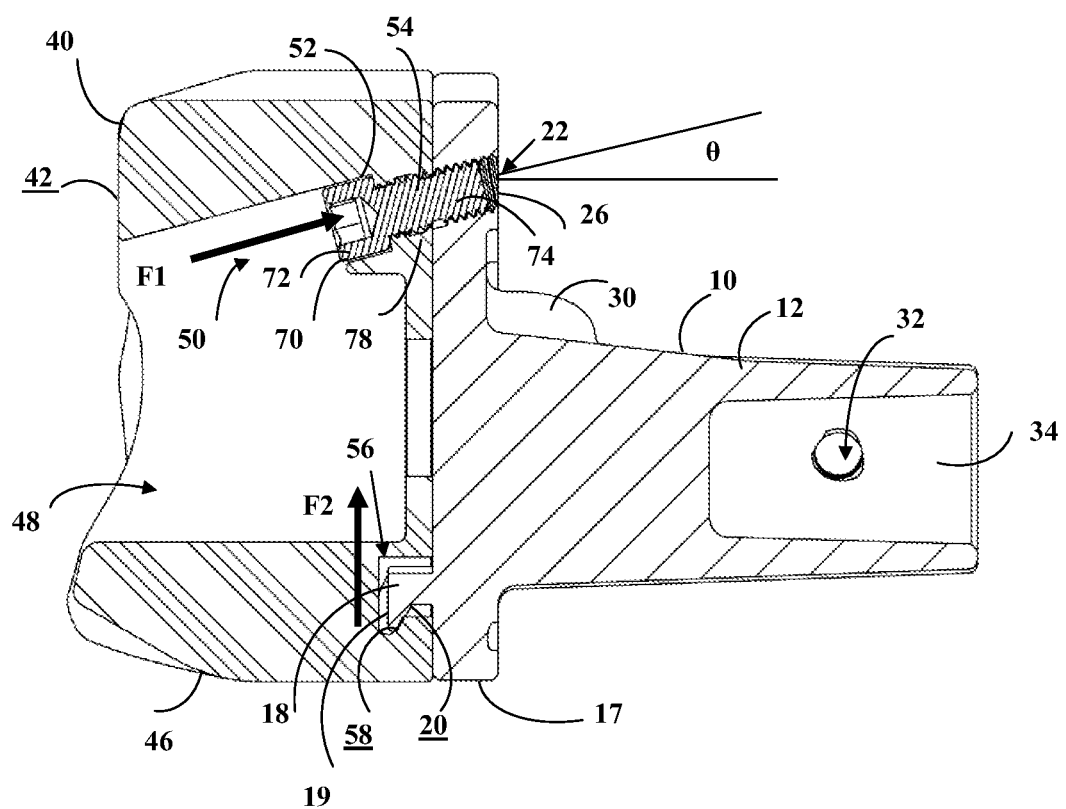
Figure 9:
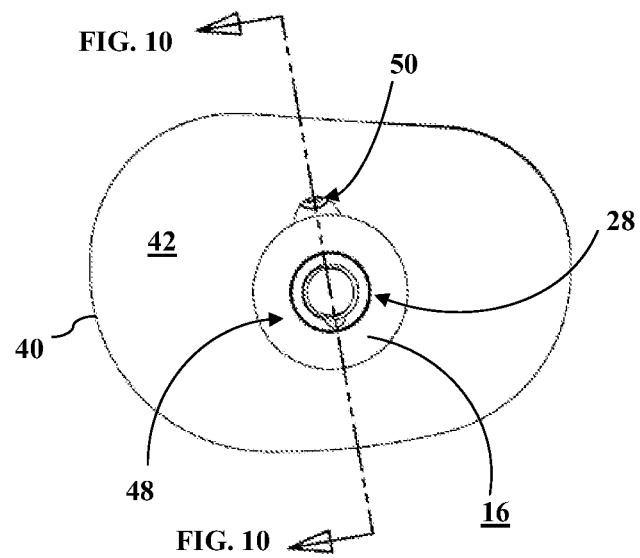
FIG. 9 is a top plan view of another assembly comprising a fixed insert, a tibial component, and a fastener.
Figure 10:
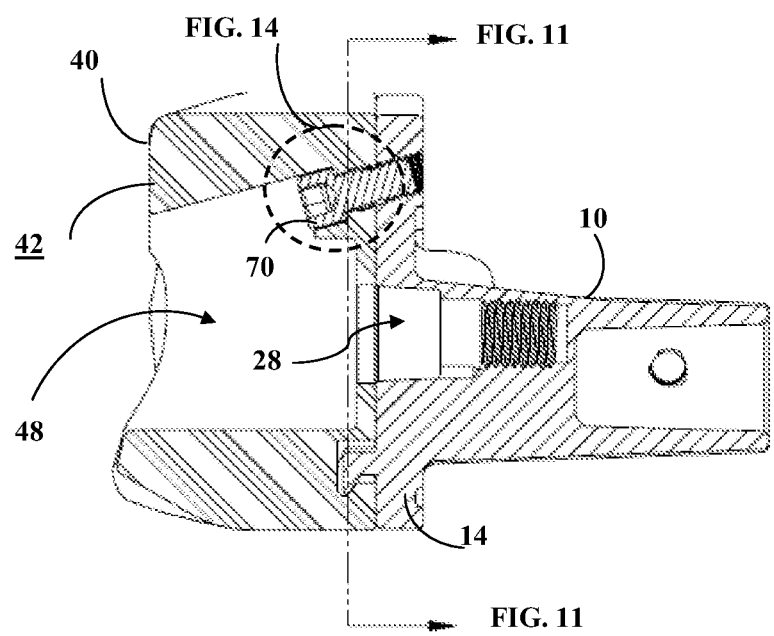
FIG. 10 is a cross-sectional view of the assembly of FIG. 9 taken along line FIG. 10-FIG. 10.
Figure 11:
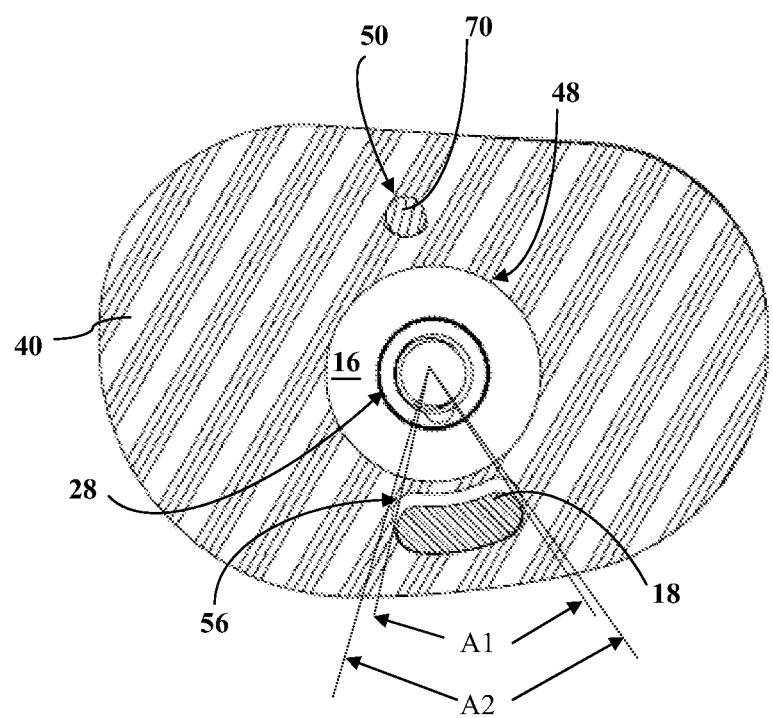
FIG. 11 is a cross-sectional view of the assembly of FIG. 10 taken along line FIG. 11-FIG. 11.
Figure 15:
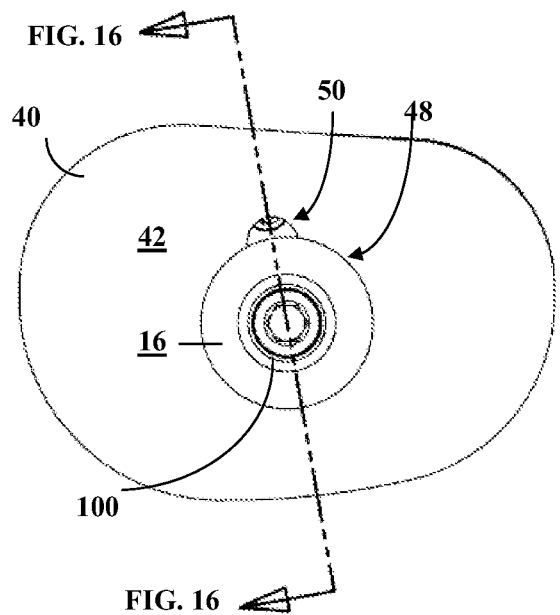
FIG. 15 is a top plan view of another assembly including a fixed insert, a tibial component, a fastener, and a post.
Figure 16:
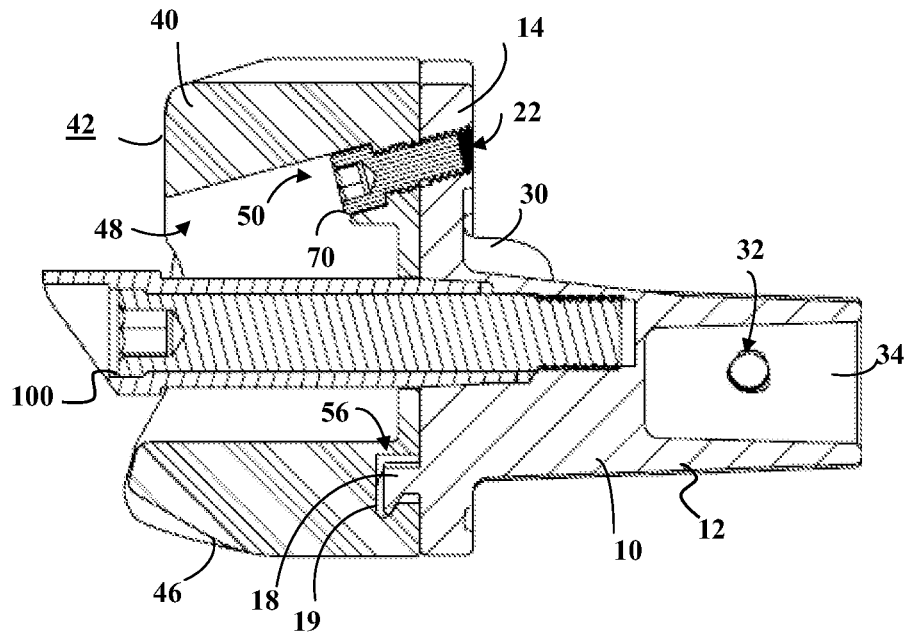
FIG. 16 is a cross-sectional view of the assembly of FIG. 15 taken along line FIG. 16-FIG. 16.
Figure 17:
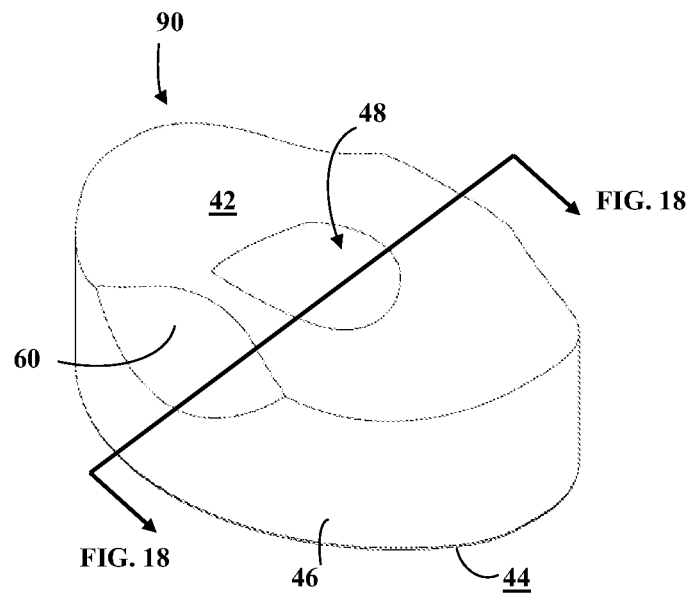
FIG. 17 is a perspective view of a rotatable insert.

As shown in FIGS. 1-2, the tibial component 10 includes an opening 28 to receive a post 100 (see FIG. 16). Posts 100 may be used with either rotatable inserts 90 (as shown in FIGS. 19-23) or with fixed inserts 40 (as shown in FIGS. 15 and 16). It should be understood that post 100 is not a necessity for the functionality of fixed insert 40. But if fixed insert 40 is used in an orthopaedic implant incorporating a hinge design, then post 100 may be provided to connect a femoral component (not shown) to the tibia. In some embodiments, post 100 may be used to capture, constrain or secure a femoral implant to the tibial implant, while still allowing for certain desired articulations, rotations, and/or other movements between the femoral and tibial implants. Even when the tibial component 10 is provided with an opening 28 it is not necessary to provide a post 100. Rather, opening 28 may remain vacant in some uses, as shown in FIGS. 9-11. In still other embodiments the tibial component 10 does not include such an opening 28 (such as in FIGS. 8A and 8B). It should be understood that the opening 28 is non-limiting and is not required for all embodiments; however, it may be preferred to provide a tibial component 10 with an opening 28 such that a surgeon may decide interoperatively whether to use a post 100.

As illustrated in FIGS. 1-2, certain embodiments of the tibial component 10 include a retaining tab 18 having a hooked edge 19. The retaining tab 18 may be set back from the anterior edge 17 of the tibial tray 14 such that the tab 18 is not exposed to the patient's anatomy when implanted. As described in more detail herein, the retaining tab 18 acts as a "hook" to couple the tibial insert 40, 90 to the tibial component 10. In one embodiment at least a portion of the hooked edge 19 may include an angled surface 20. The angled surface 20 may be provided on the entire length of the hooked edge 19, or only a portion of the length. The particular angle $\beta$ of the angled surface 20 (see FIG. 2) may vary between embodiments and is not limiting. In certain embodiments the hooked edge 19 does not have an angled surface 20, such that the hooked edge 19 is generally parallel to the tray surface 16 of the tibial tray 14.

In some embodiments, the retaining tab 18 could be part of a tibial insert 40, 90 rather than the tibial component 10, and the tibial component 10 could include structure for interacting with the retaining tab 18 (described below). In these or other embodiments, the retaining tab 18 does not necessarily have to be hooked-shaped (or be a tab) to accomplish the functions set forth herein.

The tibial component 10 may also be provided with an angled opening 22 to receive a fastener 70. As shown in FIG. 2, angled opening 22 is angled by angle $\theta$ with respect to a perpendicular line from the tibial tray 14. Although the angle $\theta$ may vary between different embodiments, the magnitude of the angle $\theta$ may be constrained by the size of the tibial tray 14. For example, smaller tibial trays 14 may have a smaller angle $\theta$ than larger tibial trays 14. In certain embodiments the angled opening 22 includes threads 26 (to mate with threads 76 of the fastener 70) and a counterbore portion 24. Counterbore portion 24 is not required, but may be provided in order to more easily machine threads 26 into the angled opening 22. As described in more detail herein, the angled opening 22 helps to provide a more secure connection between the fixed tibial insert 40 and the tibial component 10.

The tibial component 10 may be made of any suitable material, including either metal (such as but not limited to titanium, oxidized zirconium, surgical stainless steel, or others), plastics (such as but not limited to high molecular weight polyethylene (either cross-linked or not cross-linked)), ceramics, other materials, or combinations of these or other materials. If desired, the tibial component 10 may be porous or coated with material (such as hydroxyapatite) to increase fixation of the tibial component 10 within the bone. In general the material and surface treatments of the tibial component 10 are non-limiting.

FIGS. 3-16 show a fixed insert 40 for connection to a tibial component. The fixed insert 40 may be coupled to the tibial component 10 such that there is little to no rotation between the fixed insert 40 and the tibial component 10. The fixed insert 40 may include a superior surface 42 that is shaped to provide an articular surface or surfaces for the condyles of a femoral component (not shown) and/or the native femur. An inferior surface 44 may be provided opposite the superior surface 42, and is generally planar (in the embodiment shown) to contact the tray surface 16 of the tibial tray 14. Sidewalls 46 extend between the superior surface 42 and the inferior surface 44. The height of the sidewalls 46 (and consequentially the thickness of the fixed insert 40) may vary between embodiments and is in no way limiting.

In certain embodiments the fixed insert 40 is provided with a central opening 48 and an angled opening 50. The angled opening 50 may include a counterbore portion 52 and a threaded portion 54. As shown in FIGS. 8A-B, a fastener 70 may be inserted into the angled openings 50, 22 of the fixed insert 40 and the tibial component 10. Thus, as shown in FIG. 8A, the angles θ of both angled openings 50, 22 are approximately equal. The central opening 48 provides access to the angled opening 50 such that the surgeon has room to insert and secure the fastener 70. Also, if it is desired to use a post 100 (such as in FIGS. 15 and 16), the central opening 48 provides room for the post 100.

Figure 5:
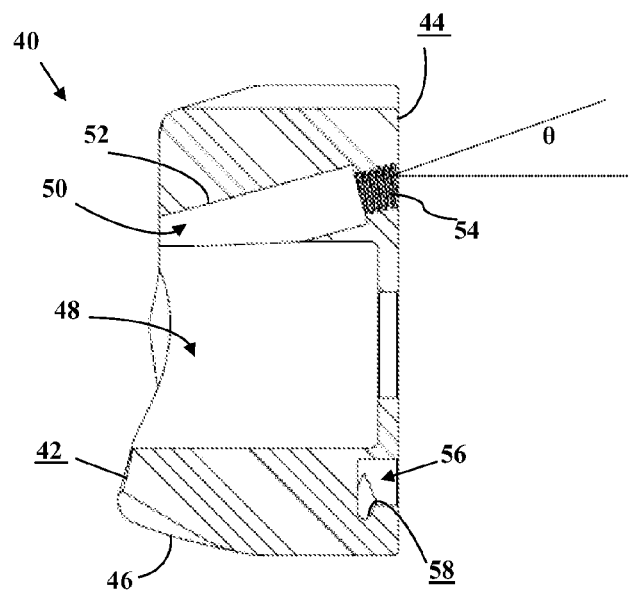
FIG. 5 is a cross-sectional view of the fixed insert of FIG. 4 taken along line FIG. 5-FIG. 5.
Figure 6:
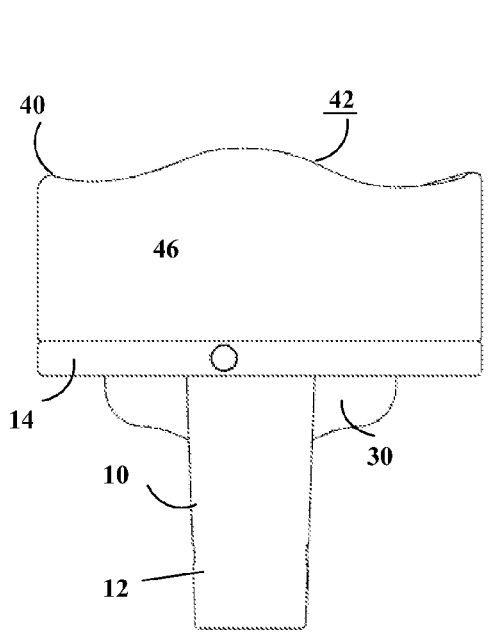
FIG. 6 is a front view of an assembly comprising a fixed insert, a tibial component, and a fastener.
Figure 7:
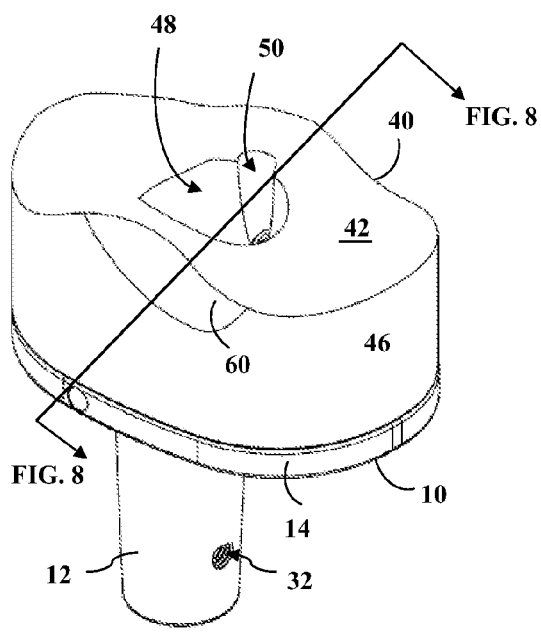
FIG. 7 is a perspective view of the assembly of FIG. 6.

As shown in FIG. 5, in certain embodiments the fixed insert 40 includes a tab opening 56. As shown in FIGS. 8A-B, the tab opening 56 receives the retaining tab 18 of the tibial component 10. If the hooked edge 19 of the retaining tab 18 includes an angled surface 20, then the tab opening 56 may also include an angled surface 58. Otherwise, both the hooked edge 19 and the tab opening 56 can be substantially parallel to the tray surface 16 (and will not have angled surfaces 20, 58). As mentioned above, in other embodiments, tabs 18 and tab openings 56 can have other shapes and configurations.

FIGS. 8A and 8B both show an assembly comprising a tibial component 10, a fixed insert 40, and a fastener 70. In FIG. 8A the fastener 70 is inserted through the angled opening 50 of the fixed insert 40. As shown in FIG. 8B, when the fastener 70 is seated in the opening 50 with its head 72 bearing against the shoulder of counterbore 52 and the threads 76 engaged with the threaded portion 26 of opening 22, fastener 70 can exert a compressive force F1 between the tibial component 10 and the fixed insert 40 along the angle θ. Because force F1 is non-perpendicular to the tibial component 10 and fixed insert 40, a component of this force will act on the fixed insert 40 in an anterior to posterior direction, as indicated by force F2 in FIG. 8B. Thus, the fixed insert 40 may be drawn (or at least disposed) in the direction of the force F2, which causes the angled surface 58 of the tab opening 56 to contact and press against the angled surface 20 of the retaining tab 18. Thus, a wedge-like effect may be effected between the angled surfaces 20, 58 of the tab opening 56 and the retaining tab 18. This wedge effect securely fastens the fixed insert 40 to the tibial component 10 such that vertical separation (or pull out) between the fixed insert 40 to the tibial component 10 is minimized or eliminated, and, in some embodiments, may also help to minimize or eliminate the tendency of the fixed insert 40 to rotate with respect to tibial component 10. Additionally, and as discussed in more detail below, the engagement between the fastener 70 and the angled openings 22, 50 also prevents vertical separation. Rotation between the fixed insert 40 and the tibial component 10 may be further minimized in some embodiments due to the close fit between the tab opening 56 and the retaining tab 18. Specifically, as shown in FIG. 11, the projected angles of the tab opening 56 (A2) and the retaining tab 18 (A1) are approximately equal such that there is a close fit between the two components, leaving the fixed insert 40 with little (if any) room to rotate.

As shown in FIGS. 8A and 8B, the retaining tab 18 is set back from the anterior edge 17 of the tibial component 10. When assembled, a portion of the fixed insert 40 covers the retaining tab 18 such that neither the retaining tab 18 or the tab opening 56 are exposed to the patient's surrounding anatomy.

Figure 12:
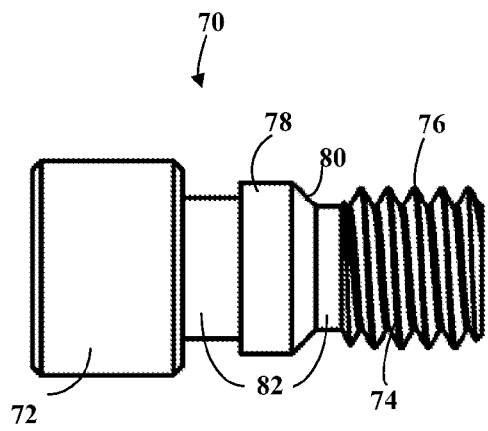
FIG. 12 is a side view of a fastener.
Figure 13:
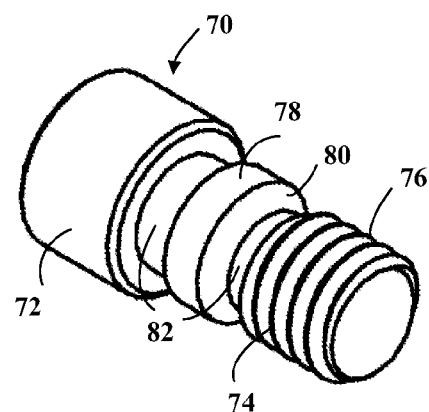
FIG. 13 is a perspective view of the fastener of FIG. 12.
Figure 14:
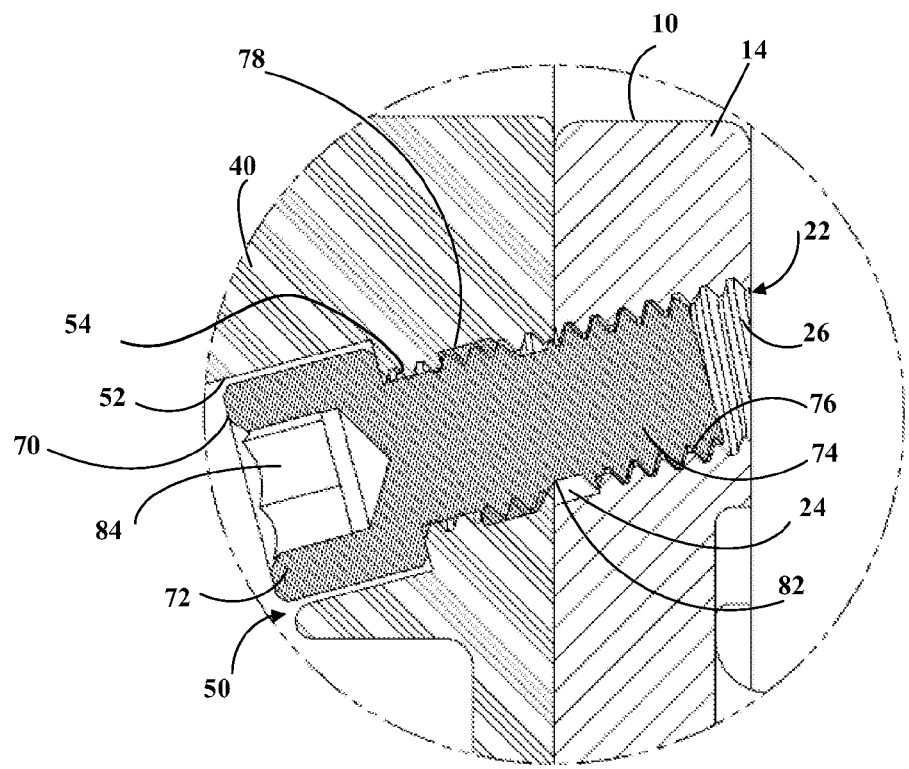
FIG. 14 is a detail view of the assembly of FIG. 10.

FIGS. 12-14 illustrate a fastener 70 with structure to more securely fasten the fixed insert 40 to the tibial component 10. Fastener 70 may include a shaft 74 with a threaded portion 76 and an interference portion 78 along at least a portion of its length. Optionally, the fastener 70 may include a head 72. As shown in FIG. 14, the fastener 70 may also be provided with a counterbore 84 to receive a driver.

If desired, the threaded portion 76 (and/or the female threads of the aperture in which the fastener 70 is used) may incorporate threads such as the SPIRALOCK® thread made by Emhart Teknologies (based in Shelton Conn.), or threads as described in (inter alia) U.S. Pat. Nos. 4,171,012, 4,150, 702, or 4,076,064. Such threads incorporate a wedge ramp design that distributes the loads of the threaded joint more evenly throughout all of the engaged threads, and also minimizes loosening under vibration. But it should be understood that such threads are not required, and the threaded portion 76 may incorporate any type of standard thread.

Together with the threaded portion 76, or by itself, a means for creating an interference fit (e.g. the interference portion 78) may act to minimize loosening and pull-out of the fastener 70. The interference portion 78 may be provided anywhere along the length of the fastener 70, and may be provided in many different shapes, lengths, or diameters. For example, in FIGS. 12 and 13 the interference portion 78 has approximately the same diameter as the major diameter of the threaded portion 76. In other embodiments the interference portion 78 may have a smaller or larger diameter. If desired, the interference portion 78 may include a chamfer 80. In certain embodiments the interference portion 78 is separated by the threaded portion 76 and the head 72 (respectively) by necks 82. But the necks 82 are not required; for example, in another embodiment the interference portion 78 could contact the threaded portion 76.

FIG. 14 is a detail view of a fastener 70 secured within angled openings 22, 50. The threaded portion 76 of the fastener 70 threadedly engages with the threaded portions 26, 54 of the tibial component 10 and the fixed insert 40, respectively. As the fastener 70 is drawn further within angled opening 50, an interference fit is created between the interference portion 78 and the threads 54 or other portions of the angled opening 50. It may be desirable to create an interference fit through more than one turn of the fastener 70. In certain embodiments the threads 54 cut into and/or otherwise deform the interference portion 78. In other embodiments the interference portion 78 may cut into and/or otherwise deform the threads 54 (or other portions of a threaded or non-threaded opening) In still other embodiments both the threads and the interference portion 78 are deformed. The selection of materials for the threads 54 and the interference portion 78 may determine which of the components becomes deformed. Upon deformation, the fastener 70 becomes securely fixed within the angled opening 50 of the fixed insert 40. Embodiments of fasteners 70 have been found to remain securely fastened within one or both of the angled openings 22, 50 and/or resistant to back-out even if a portion of the threads 26, 54, 76 become loosened or if fastener 70 rotates in the openings 22, 50.

In other embodiments, the fastener 70 or the openings 22, 50 may be provided with still additional or alternative structure by which to create an interference fit within the angled openings 22, 50. For example, the threaded portion 76 of the fastener 70 could be provided with threads having a different pitch than the threaded portion 54 of the fixed insert 40 (or of the threaded portion 26 of the tibial component 10). The different pitched threads create an interference fit. As other examples, the fastener 40 and/or the openings 22, 50 may be provided with structure other than threads (such as barbs, ribbing, dove-tails, or any other shape) that would create an interference fit.

Figure 14A:
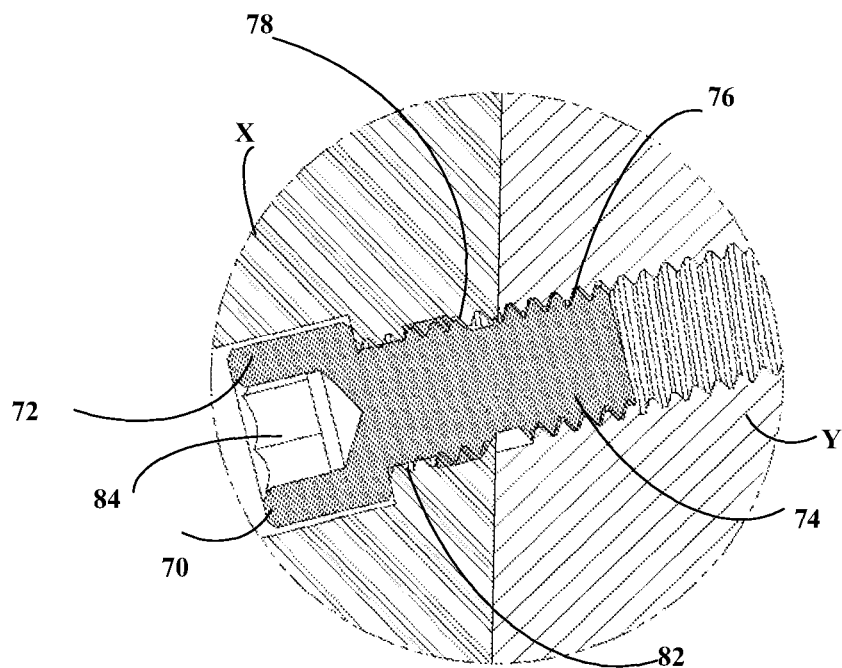
FIGS. 14A and 14B are detailed views of another assembly including a fastener.
Figure 14B:
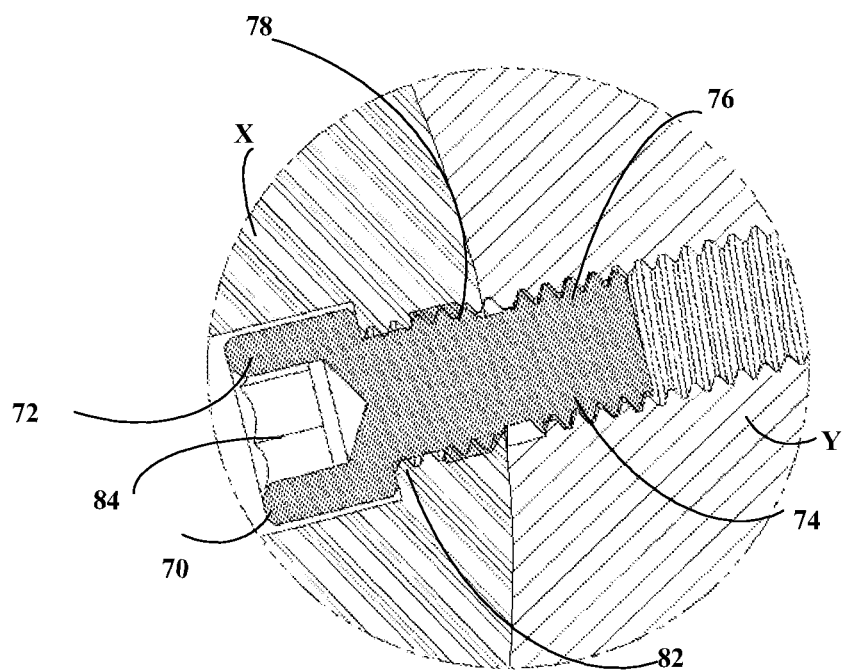

In other embodiments, fastener 70 may be used in contexts other than coupling the fixed insert 40 to the tibial component 10. For example, fastener 70 may be used to couple any two components together relating to any other implant, joint, or anatomy. Non-limiting examples include coupling the following components together: an acetabular cup and a shell, a bone plate and bone, a glenoid and a base, a unicondylar insert and a unicondylar base, or a non-hinge insert and a tibial base. Thus, FIGS. 14A and 14B are detailed views of fastener 70 in use with such other applications, where the reference number "X" generally refers to a first component and reference number "Y" generally refers to a second component. In FIG. 14A the contact between components X, Y is generally planar, such as might be seen when coupling a bone plate to bone. In FIG. 14B the contact between components X, Y is curved, such as might be seen when coupling a cup and a shell.

Figure 18:
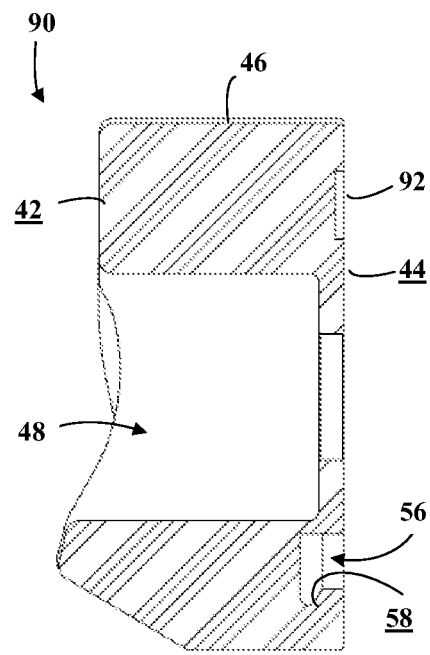
FIG. 18 is a cross-sectional view of the rotatable insert of FIG. 17 taken along line FIG. 18-FIG. 18.
Figure 19:
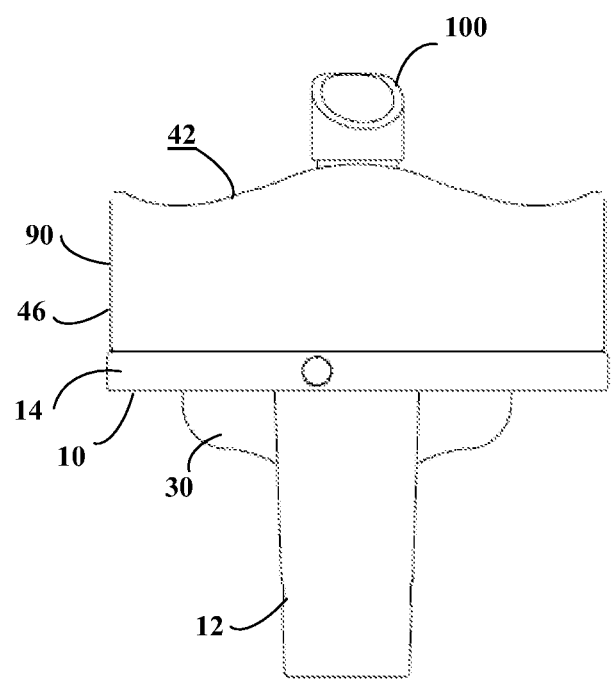
FIG. 19 is a side view of an assembly comprising a rotatable insert, a tibial component, and a post.
Figure 20:
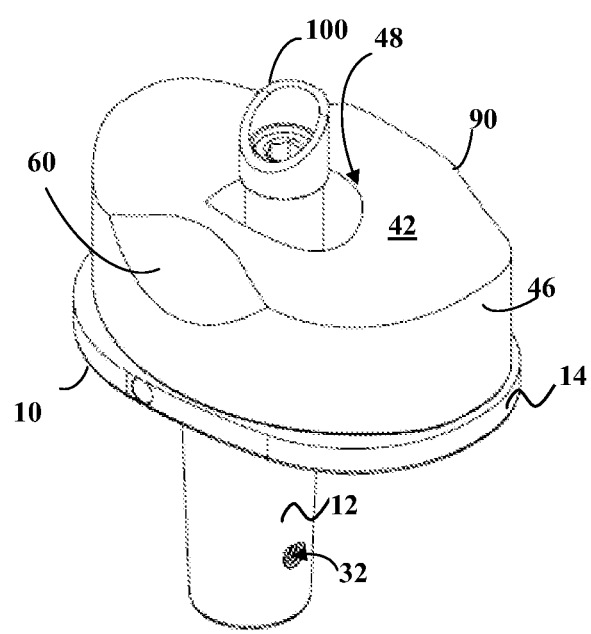
FIG. 20 is a perspective view of the assembly of FIG. 19.
Figure 21:
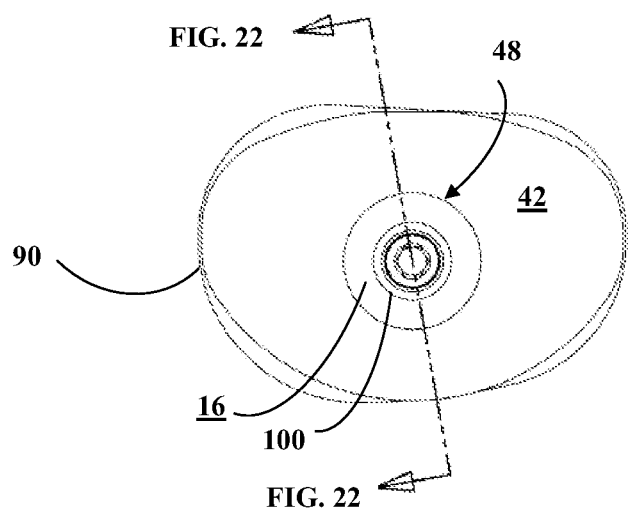
FIG. 21 is a top plan view of the assembly of FIG. 20.

FIGS. 17-23 show a rotatable insert 90. Rotatable insert 90 rotates with respect to the tibial component 10 during at least some portions of flexion and extension of the knee joint. As shown in FIG. 18, rotatable insert 90 may include a superior surface 42 that is shaped to contact condyles of a femoral component and/or a native femur (not shown). An inferior surface 44 may be provided opposite the superior surface 42 to contact the tray surface 16 of the tibial tray 14. The inferior surface 44 may be provided with a recess 92 that is generally aligned with the angled opening 22 of the tibial component 10. The recess 92 may be provided in order to avoid any contact between the inferior surface 44 of the rotatable insert 90 and any sharp edges or burrs that might be present adjacent to opening 22. Such contact may produce undesirable debris. It should be understood that the recess 92 is optional, and is not required for any embodiments. Sidewalls 46 extend between the superior surface 42 and the inferior surface 44. The height of the sidewalls 46 (and consequentially the thickness of the rotatable insert 90) may vary between embodiments and is in no way limiting. In certain embodiments the rotatable insert 90 is provided with a central opening 48.

Figure 22:
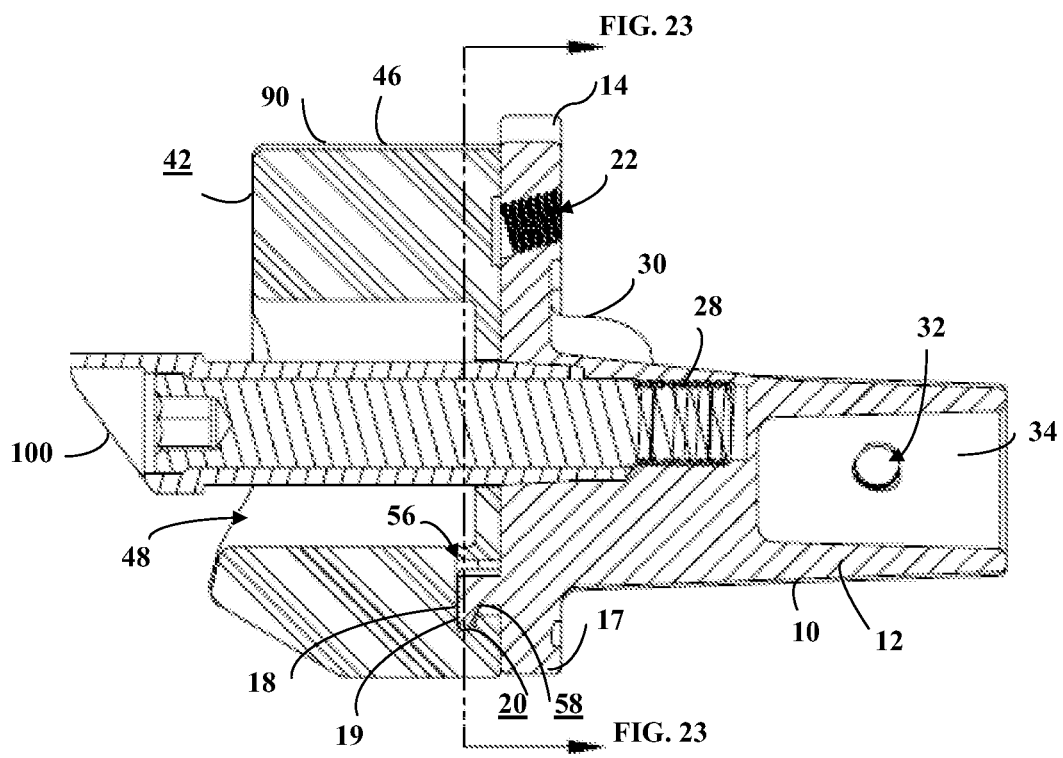
FIG. 22 is a cross-sectional view of the assembly of FIG. 21 taken along line FIG. 22-FIG. 22.

FIGS. 19-23 show an assembly comprising a tibial component 10, a rotatable insert 90, and a post 100. As shown in FIG. 22, the tab opening 56 of the rotatable insert 90 receives the retaining tab 18 of the tibial component 10. If the hooked edge 19 of the retaining tab 18 includes an angled surface 20, then the tab opening 56 may also include an angled surface 58. Otherwise, both the hooked edge 19 and the tab opening 56 can be substantially parallel to the tray surface 16 or positioned in other configurations. The rotatable insert 90 shown is constrained from vertical separation (thus preventing pull-out) by the contact between the hooked edge 19 and the tab opening 56. At the same time, irritation to the patient's surrounding anatomy is lessened because the retaining tab 18 is set back from the anterior edge 17 of the tibial component 10 such that a portion of the rotatable insert 90 covers the retaining tab 18. Thus, neither the retaining tab 18 or the tab opening 56 are exposed to the patient's surrounding anatomy.

A post 100 may be received within the openings 48, 28 of the rotatable insert 90 and the tibial component 10, respectively. A lower portion of the opening 48 in insert 90 may at least roughly correspond to the outer diameter of post 100, thus fixing the translational positioning of the insert 90 on the tibial component 10, while still allowing the insert 90 to rotate with respect to the tibial component 90.

Figure 23:
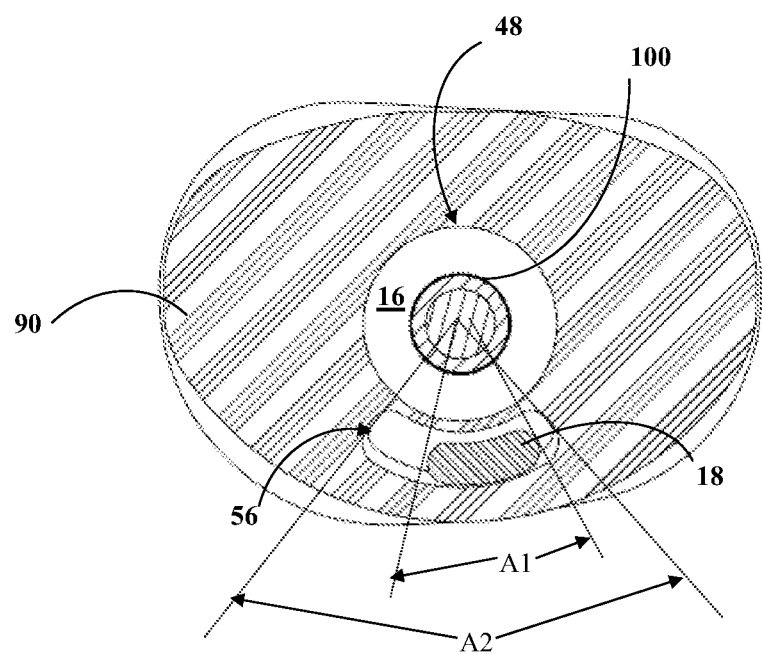
FIG. 23 is a cross-sectional view of the assembly of FIG. 22 taken along line FIG. 23-FIG. 23.

As shown in FIG. 23, the interaction between the retaining tab 18 and tab opening 56 allows some rotation of the rotatable insert 90 (unlike the fixed insert 40 embodiment described above) because the tab opening 56 extends along a greater portion of a rotational arc (defined by a radius extending from the center of rotation of the insert 90) than the retaining tab 18. Specifically, the projected angle of tab opening 56 (A2) is greater than the projected angle of the retaining tab 18 (A1). Thus, the rotatable insert 90 may rotate by an angle equal to the difference between the projected angles A2 and A1. But the rotatable insert 90 is constrained from excessive rotation when the retaining tab 18 contacts the tab opening 56. Additionally, the interaction between retaining tab 18 and tab opening 56 helps to resist pull out of the insert 90 from the tibial component 10 in a similar manner to that described above for the fixed insert 40 (although that resistance may be somewhat lessened in this particular embodiment since an angled fastener 70 is not necessarily used).

The fixed insert 40 and/or the rotatable insert 90 may be made of any suitable material, including either metal (such as but not limited to titanium, oxidized zirconium, surgical stainless steel, or others), plastics (such as but not limited to high molecular weight polyethylene (either cross-linked or not cross-linked)), ceramics, other materials, or combinations of these or other materials. If desired, the inserts 40, 90 may be polished, coated, or have other surface treatments. In general the material and surface treatments of the inserts 40, 90 are non-limiting.

The foregoing is provided for purposes of illustration and disclosure of embodiments of the invention. It will be appreciated that those skilled in the art, upon attaining an understanding of the foregoing may readily produce alterations to, variations of, and equivalents to such embodiments. For example, although the orthopaedic implants have generally been described as a knee joint replacement, the same concepts could be applied to orthopaedics for other joints or other implants. Accordingly, it should be understood that the present disclosure has been presented for purposes of example rather than limitation, and does not preclude inclusion of such modifications, variations and/or additions to the present subject matter as would be readily apparent to one of ordinary skill in the art.

The invention claimed is:

1. A tibial implant comprising a first implant component, the first implant component comprising:
   a. a substantially planar mounting surface configured for mounting to a second implant component;
   b. a retaining tab fixed to and extending upwardly away from the substantially planar mounting surface, the retaining tab having a hooked edge and being bordered on a posterior side by the substantially planar mounting surface such that a portion of the substantially planar mounting surface abuts and extends posteriorly from the posterior side; and c. an angled opening defined through the substantially planar mounting surface, the angled opening being configured to receive a fastener to secure the first implant component to a second implant component, wherein the angled opening extends at an angle that is non-perpendicular relative to the substantially planar mounting surface.

2. The tibial implant of claim 1, wherein the angled opening is angled away from the retaining tab.

3. The tibial implant of claim 2, wherein the angled opening is at least partially threaded.

4. The tibial implant of claim 2, wherein the mounting surface has an outer perimeter, and the retaining tab is set back from the outer perimeter of the mounting surface.

5. The tibial implant of claim 1, wherein the hooked edge extends anteriorly and the angled opening extends posteriorly.

6. The tibial implant of claim 1, wherein the retaining tab comprises a substantially vertical portion and wherein the hooked edge extends from an upper end of the substantially vertical portion.

7. The tibial implant of claim 6, wherein the hooked edge is substantially horizontal relative to the substantially vertical portion.

8. The tibial implant of claim 7, wherein the retaining tab includes an angled surface on an underside of the hooked edge.

9. The tibial implant of claim 1, wherein the first implant component comprises a tibial tray.

10. The tibial implant of claim 9, further comprising a second implant component, wherein the second implant component comprises a tibial insert, the tibial insert comprising an articular surface on a superior side of the tibial insert and a substantially planar mounting surface on an inferior side of the tibial insert.

11. The tibial implant of claim 10, wherein the tibial insert further comprises a tab opening configured to receive the retaining tab, the tab opening extending into the substantially planar mounting surface of the tibial insert.

12. The tibial implant of claim 11, wherein the tab opening further comprises an angled surface configured to confront an angled surface of the retaining tab.

13. The tibial implant of claim 12, wherein the tibial insert comprises an angled opening configured to receive the fastener, wherein the angled opening of the tibial insert extends away from the substantially planar mounting surface of the tibial insert, and at the same angle as the angled opening of the first implant component extends relative to the substantially planar mounting surface of the first implant component.

14. The tibial implant of claim 13, further comprising the fastener, wherein the fastener includes an interference portion configured to cause an interference fit with respect to at least one of the angled openings of the first implant component and the tibial insert.

15. The tibial implant of claim 1, further comprising
a second implant component comprising an articular surface, a mounting surface opposite the articular surface, and a tab opening defined on the mounting surface and at least partially extending into the second implant component,
wherein the tab opening is configured to receive the retaining tab such that the mounting surface of the first implant component contacts the mounting surface of the second implant component, and
wherein the retaining tab is configured to rotate in the tab opening along a rotational arc.

16. The tibial implant of claim 1, wherein the retaining tab comprises a vertical portion that extends in a generally superior direction from the substantially planar mounting surface, and wherein the hooked edge extends from the vertical portion and anterior to the vertical portion.

17. The tibial implant of claim 16, wherein the vertical portion has an anterior side, and wherein the hooked edge and the substantially planar mounting surface define a gap that extends medially and laterally along the anterior side of the vertical portion.

18. The tibial implant of claim 1, wherein the angled opening is located posterior to the retaining tab.

19. A tibial implant comprising:
a. a tibial tray, wherein the tibial tray comprises a substantially planar tray surface and an angled opening configured to receive a fastener, wherein the angled opening extends downwardly through the substantially planar tray surface at an angle that is non-perpendicular relative to the substantially planar tray surface; and
b. a tibial insert, wherein the tibial insert comprises an articular surface and a substantially planar mounting surface configured to abut the tray surface;
wherein a retaining tab including a hooked edge extends from one of the tray surface and the mounting surface;
wherein a tab opening including a recess extends into the other of the tray surface and the mounting surface, the recess being bounded by the other of the tray surface and the mounting surface; and
wherein the hooked edge of the retaining tab is configured to engage the recess of the tab opening and the recess is configured to receive the retaining tab such that the retaining tab is not exposed when the tibial insert is mounted to the tibial tray with the substantially planar mounting surface of the tibial insert in abutment with the tray surface of the tibial tray.

20. The tibial implant of claim 19, wherein the tibial insert is a mobile bearing insert and wherein the substantially planar mounting surface is a second articular surface.

21. The tibial implant of claim 19, wherein the tibial insert is a fixed insert; and wherein the tibial implant further comprises the fastener configured to be received in the angled opening.

22. The tibial implant of claim 19, wherein the retaining tab extends from the tray surface; and wherein the hooked edge of the retaining tab and the angled opening extend away from one another.

23. The tibial implant of claim 19, wherein the other of the tray surface and the mounting surface surrounds the recess of the tab opening.

24. The tibial implant of claim 19, wherein the recess of the tab opening is defined to have a shape complementary to the hooked edge of the retaining tab.

25. The tibial implant of claim 24, wherein the hooked edge has an angled surface, and the tab opening is defined in part by a corresponding angled surface configured to engage the angled surface of the hooked edge.

26. A tibial implant, comprising:
a. a first orthopaedic component, the first orthopaedic component including an articular surface and a mating surface, wherein a first opening extends from the mating surface of the first orthopaedic component at least partially through the first orthopaedic component;
b. a second orthopaedic component, the second orthopaedic component including a mating surface configured to abut the mating surface of the first orthopaedic component, wherein a second opening extends from the mating surface of the second orthopaedic component at least partially through the second orthopaedic component, wherein the second opening is an angled opening defined through the mating surface of the second orthopaedic component; and c. a threaded fastener configured to secure the first orthopaedic component to the second orthopaedic component and to extend at least partially through the first and second openings, wherein the fastener includes a deformable portion for creating an interference fit with at least one of the first and second openings;

wherein at least one of the first and second openings is partially threaded, and the deformable portion is configured to deform by engagement with threads of at least one of the first and second openings;

wherein the mating surface of the first orthopaedic component or the second orthopaedic component defines a recess, and a retaining tab including a hooked edge extends from the mating surface of the other of the first orthopaedic component or the second orthopaedic component; and wherein the recess is configured to receive the retaining tab such that the retaining tab is not exposed when the retaining tab is positioned in the recess and the mating surface of the first orthopaedic component engages the mating surface of the second orthopaedic component.

27. The tibial implant of claim 26, wherein the first opening and the second opening extend posteriorly in an inferior direction.

28. A tibial implant comprising a first implant component, the first implant component comprising:
   a. a substantially planar mounting surface configured for mounting to a second implant component, the substantially planar mounting surface corresponding to medial and lateral condylar regions;
   b. a retaining tab located on and extending upwardly away from the substantially planar mounting surface; and
   c. an angled opening configured to receive a fastener to secure the first implant component to a second implant component, wherein the angled opening has an outer perimeter defined by the substantially planar mounting surface and the angled opening extends downwardly from the substantially planar mounting surface at an angle that is non-perpendicular relative to the substantially planar mounting surface.

29. The tibial implant of claim 28, wherein the orthopaedic component has a medial edge and a lateral edge, and the substantially planar mounting surface extends from the medial edge to the lateral edge.

30. The tibial implant of claim 28, wherein the retaining tab has a posterior edge, and the substantially planar mounting surface has a portion that extends along the posterior edge of the retaining tab and extends posteriorly from the posterior edge of the retaining tab.

* * * * *